(12) United States Patent
Orbay et al.

(10) Patent No.: US 8,764,751 B2
(45) Date of Patent: Jul. 1, 2014

(54) ENDOSTEAL NAIL PLATE FOR FIXING BONE SEGMENTS

(75) Inventors: Jorge L. Orbay, Miami, FL (US); Thomas H. Norman, Miami, FL (US); Juan Salcedo, Miami, FL (US); Ronald Litke, Shelton, CT (US)

(73) Assignee: Skeletal Dynamics, LLC, Miami, FL (US)

( * ) Notice: Subject to any disclaimer, the term of this patent is extended or adjusted under 35 U.S.C. 154(b) by 328 days.

(21) Appl. No.: 13/040,949

(22) Filed: Mar. 4, 2011

(65) Prior Publication Data

US 2011/0218531 A1 Sep. 8, 2011

Related U.S. Application Data

(60) Provisional application No. 61/310,457, filed on Mar. 4, 2010.

(51) Int. Cl.
*A61B 17/72* (2006.01)

(52) U.S. Cl.
USPC .......................................................... 606/62

(58) Field of Classification Search
USPC .......... 606/62–68, 280, 70, 71, 284, 286, 287
See application file for complete search history.

(56) References Cited

U.S. PATENT DOCUMENTS

| | | | |
|---|---|---|---|
| 3,744,488 A * | 7/1973 | Cox | 606/64 |
| 5,620,445 A * | 4/1997 | Brosnahan et al. | 606/63 |
| 2005/0102031 A1* | 5/2005 | Leonard | 623/20.21 |
| 2007/0055251 A1* | 3/2007 | Huebner et al. | 606/69 |
| 2008/0183171 A1* | 7/2008 | Elghazaly et al. | 606/64 |
| 2009/0228007 A1* | 9/2009 | Justin et al. | 606/62 |

* cited by examiner

*Primary Examiner* — Pedro Philogene
*Assistant Examiner* — David Comstock
(74) *Attorney, Agent, or Firm* — Laurence A. Greenberg; Wermer H. Stemer; Ralph E. Locher

(57) ABSTRACT

An endosteal nail plate for fixing bone segments is provided. More particularly, there is provided an endosteal nail plate that can be made up of a single piece, or of multiple pieces, as desired. Additionally, the intramedullary nail utilizes a threaded slot on the body thereof, for engaging locking screws for fixation of the intramedullary nail within a bone of a patient.

20 Claims, 12 Drawing Sheets

ENDOSTEAL NAIL PLATE FOR FIXING BONE SEGMENTS

CROSS-REFERENCE TO RELATED APPLICATIONS

The present application claims priority to: Provisional Patent Application No. 61/310,457, filed on Mar. 4, 2010 entitled "Intramedullary Nail for Fixing Bone Segments"; that application being incorporated herein, by reference, in its entirety.

FIELD OF INVENTION

The invention relates to a fixation device, and more particularly, to an endosteal nail plate for fixing diaphyseal bone segments resulting from a fracture or an osteotomy.

BACKGROUND OF INVENTION

Metallic and polymer bone plates have been used to immobilize bone segments to allow healing. These plates are typically affixed to the outer surface of the bone segments, while putting the segments in close enough proximity or contact to permit bone regrowth between the segments. One deficiency of a surface mounted plate is that it can create soft tissue irritation and impingement.

An alternative mechanism for fixing bone segments is also known wherein a mechanical device is placed within the bone segments. This type of system is commonly referred to as an intramedullary nail or rod. One of the first uses of such a rod occurred in 1939 by Gerhard Küntscher. To date, two limitations have prevented intramedullary ("IM") nails from being used more frequently. First, installing a nail that is long enough to span a gap between bone segments while providing sufficient length to attach to the bone segments typically requires insertion of the IM at the most distal or proximal ends of the bone.

Figure 1A:
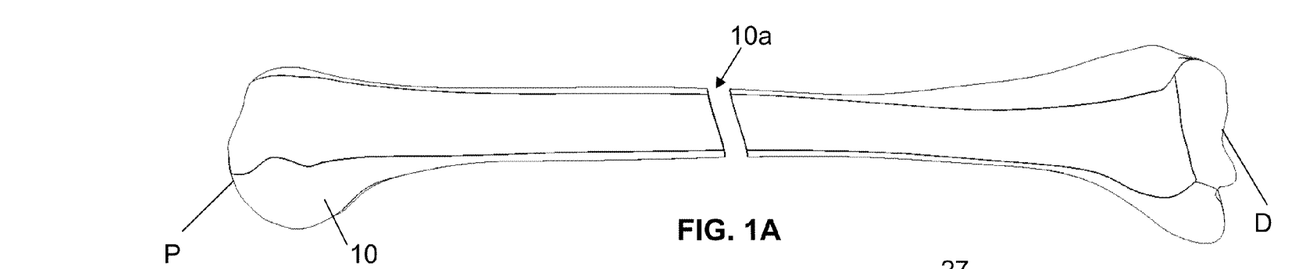
FIG. 1A is an elevational view of a bone having a fracture or osteotomy.
Figure 1B:
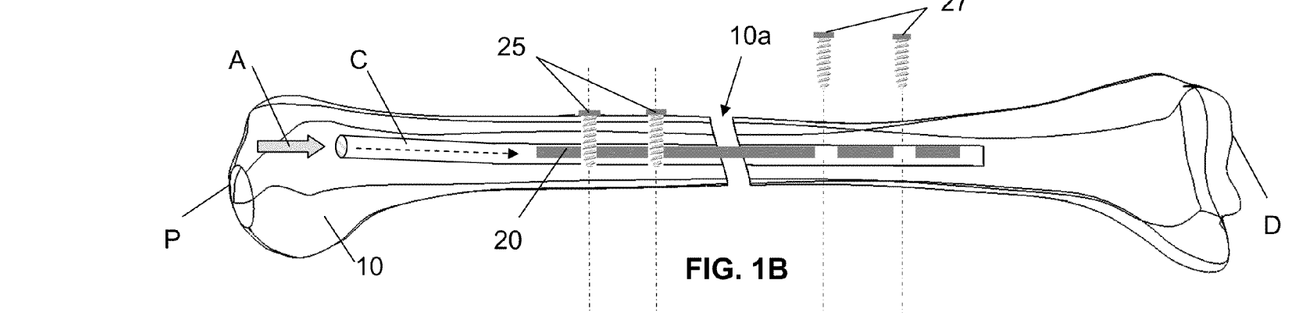
FIG. 1B is a partial cutaway view of a bone having a fracture, in which an intramedullary nail in accordance with the prior art has been inserted and the proximal end of the intramedullary nail has been fixed to the bone with locking screws.
Figure 1C:
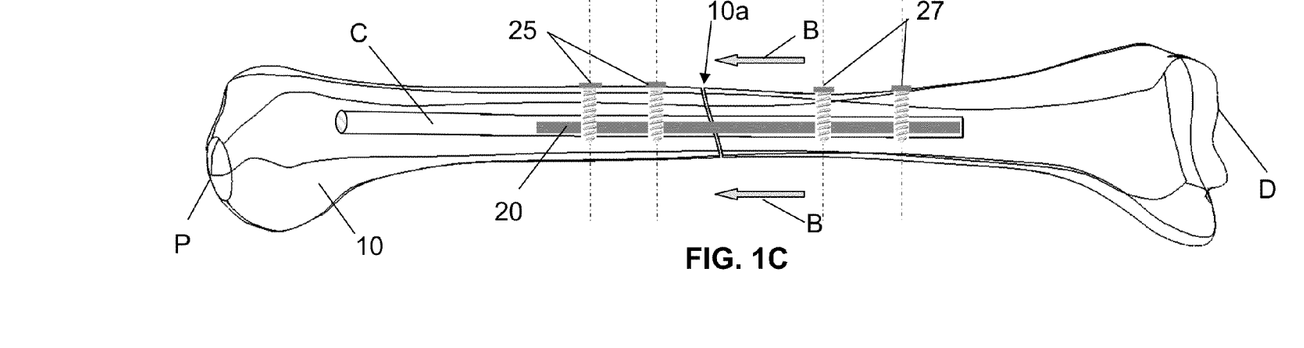
FIG. 1C is the partial cutaway view of the bone having a fracture of FIG. 1B, wherein the fracture has been reduced and the distal end of the intramedullary rod or nail has been fixed to the bone with locking screws.

For example, referring now to FIGS. 1A-1C, there is shown a bone 10 having a fracture 10a disposed between its proximal end "P" and distal end "D". In order to use the IM nail 20 of the prior art, the IM nail 20 is first inserted into the intramedullary cavity C of the bone 10, through its proximal end "P", and pushed through the intramedullary cavity in the direction of arrow "A". Once the IM nail 20 is seated in a desired position in the intramedullary cavity C (i.e., a position spanning a portion of the proximal segment of the bone, the fracture itself, and a portion of the distal segment of the bone 10), the proximal portion of the IM nail 20 is fixed to the proximal segment of the bone 10 using the locking screws 25, as shown more particularly in FIG. 1B.

Referring now to FIG. 1C, once the IM nail 20 has been fixed at the proximal end to proximal bone segment, the distal bone segment is moved in the direction of the arrow B until the fracture 10a is reduced. At this time, holes can be drilled through the distal segment of the bone 10 and the distal end of the IM nail 20 is secured to the distal segment of the bone using the locking screws 27.

A second limitation to the use of known IM nails is that it can be very difficult to adjust either the length of the IM nail (to bring the bone segments into the proper position/alignment), or to rotationally and/or angularly adjust the bone segments prior to reduction of the fracture.

Although the use of known IM nails can reduce soft tissue irritation and be less traumatic to the patient than a plate (i.e., by requiring less surgical exposure and stripping of the periosteum during implantation), they still suffer the above-discussed shortcomings.

What is needed is a device that reduces or eliminates the difficulties experienced when using known IM nails. What is further needed is a device that can provide greater adjustability and improved surgical insertion options to benefit patients with fractures or osteotomies.

SUMMARY OF THE INVENTION

It is, accordingly, an object of the instant invention to provide a device that avoids the disadvantages of the prior art. More particularly, an endosteal nail plate ("ENP") is provided that facilitates an improved placement and engagement mechanism over those used in IM nails of the prior art. In one particular embodiment of the invention, an ENP is provided that includes a threaded slot for engaging locking machine screws for fixing the device in a desired position and/or orientation and/or rotation within a bone of a patient. In another particular embodiment of the invention, the ENP is made up of a plurality of portions that can be joined by one or more connectors. In a further embodiment, one or more of the connector portions include splines, such as traditional splines, or more preferably, ("Nonius") splines as further defined herein.

Although the invention is illustrated and described herein as embodied as an endosteal nail plate for fixing bone segments, it is nevertheless not intended to be limited to only the details shown, since various modifications and structural changes may be made therein without departing from the spirit of the invention and within the scope and range of equivalents of the claims.

The construction of the invention, however, together with additional objects and advantages thereof will be best understood from the following description of the specific embodiment when read in connection with the accompanying drawings.

BRIEF DESCRIPTION OF THE DRAWINGS

For a fuller understanding of the nature of the present invention, reference should be made to the following detailed description, taken in connection with the accompanying drawings in which.

Like reference tags and/or numerals refer to like parts throughout the several views of the drawings.

DETAILED DESCRIPTION OF THE INVENTION

The instant application incorporates by reference herein U.S. patent application Ser. No. 12/561,805, now U.S. Patent Application Publication No. 2010/0130978, entitled Intramedullary Arthrodesis Nail and Method of Use, in its entirety, for all that it teaches.

Referring now to FIGS. 2-4B, an endosteal nail plate (ENP) 30 (as previously defined) for fixing bone segments is provided herein. In the present embodiment shown, the ENP 30 is formed as a single unitary piece having portions 30a, 30b and 30c. However, this is not meant to be limiting, as it should be understood that ENPs in accordance with the present invention can be made up of a single piece, or of multiple pieces, as desired. Note however, that an ENP 30 made in accordance with the present invention will include at least one threaded slot in the body thereof, which engages at least one screw 40 to fix the ENP 30 within a bone 10 of a patient. A typical screw thread has a helical spiral cut forming the thread. Traditional female attachment mechanisms have a complementary helix. An example of such a screw having a helical spiral thread is screw 40 of FIG. 3.

The ENP 30 includes a first portion 30a and a second portion 30c separated by a transitional portion 30b. The second portion 30c includes a second end 37 and at least one hole 36 for receiving a screw. Holes 36 may be threaded or non-threaded, as desired. Threaded holes 36 are adapted to receive locking machine screws, while non-threaded holes 36 are adapted to receive bicortical screws (not shown). In one particular embodiment of the invention, the holes 36 are sized and threaded to receive locking screws, such as the locking screw 40 of FIG. 3. One or more holes 34 can be provided in one or more of the portions for receiving a K-wire and/or for attachment to an alignment guide or jig (not shown), functionally similar to the alignment jig described and illustrated in U.S. Patent Application Publication No. 2010/0130978, which has been incorporated herein by reference.

Figures 2, 2A:
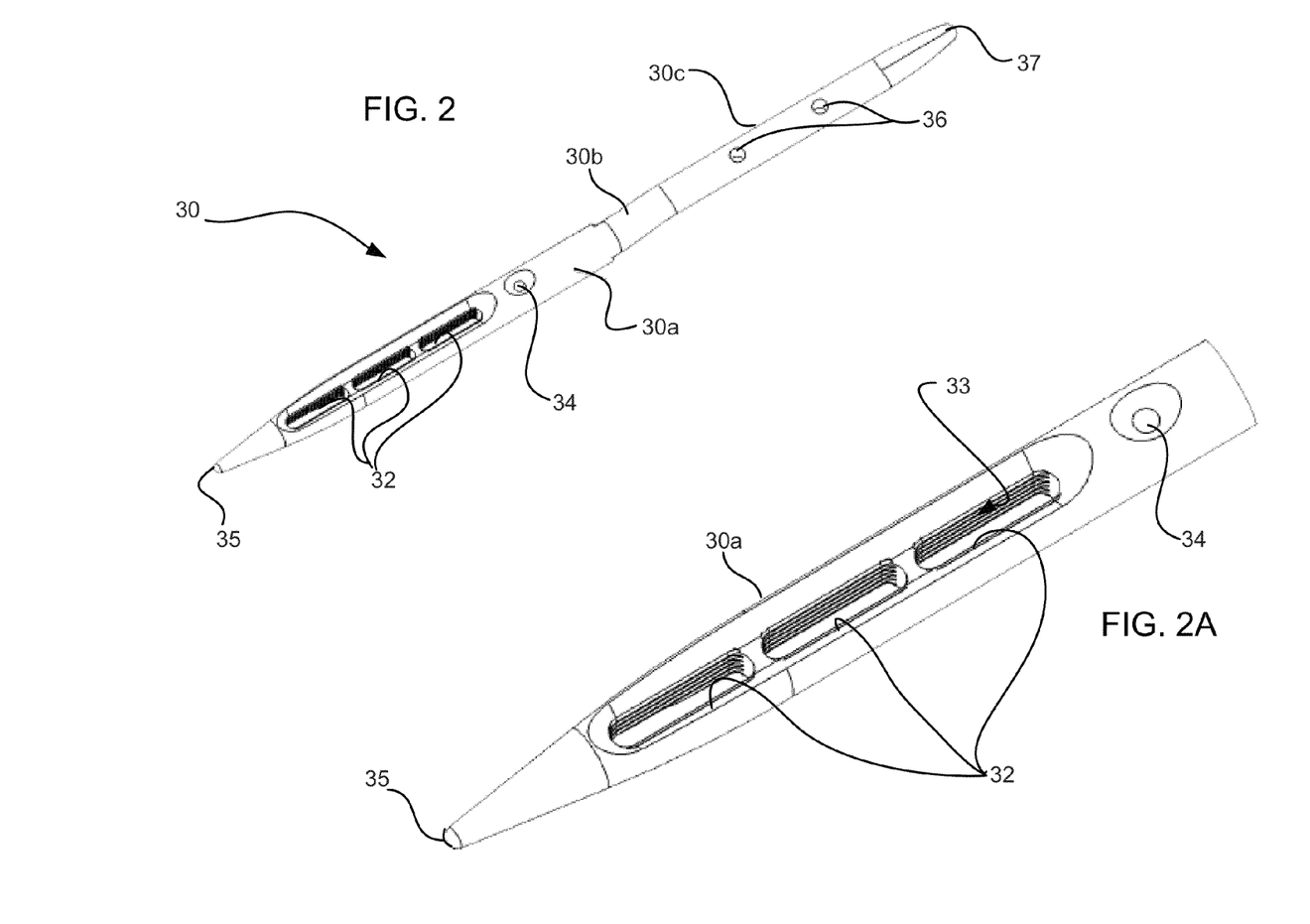
FIG. 2 is a perspective view of an endosteal nail plate in accordance with one particular embodiment of the present invention.
FIG. 2A is an enlarged view of a portion of the endosteal nail plate of FIG. 2.

Additionally, in the instant embodiment, the first portion 30a includes a first end 35, which is shown as being conical or frusto-conical, in order to assist in its placement in the intramedullary cavity 12. First portion 30a also includes at least one threaded slot 32. Although the embodiment of FIG. 2 is illustrated as including three threaded slots, this is not meant to be limiting, as fewer or more threaded slots can be provided, as desired. Spacer portions 33a and 33b separate the three threaded slots 32a, 32b and 32c of the ENP 30 of the instant embodiment.

Figures 2B, 2C, 3:
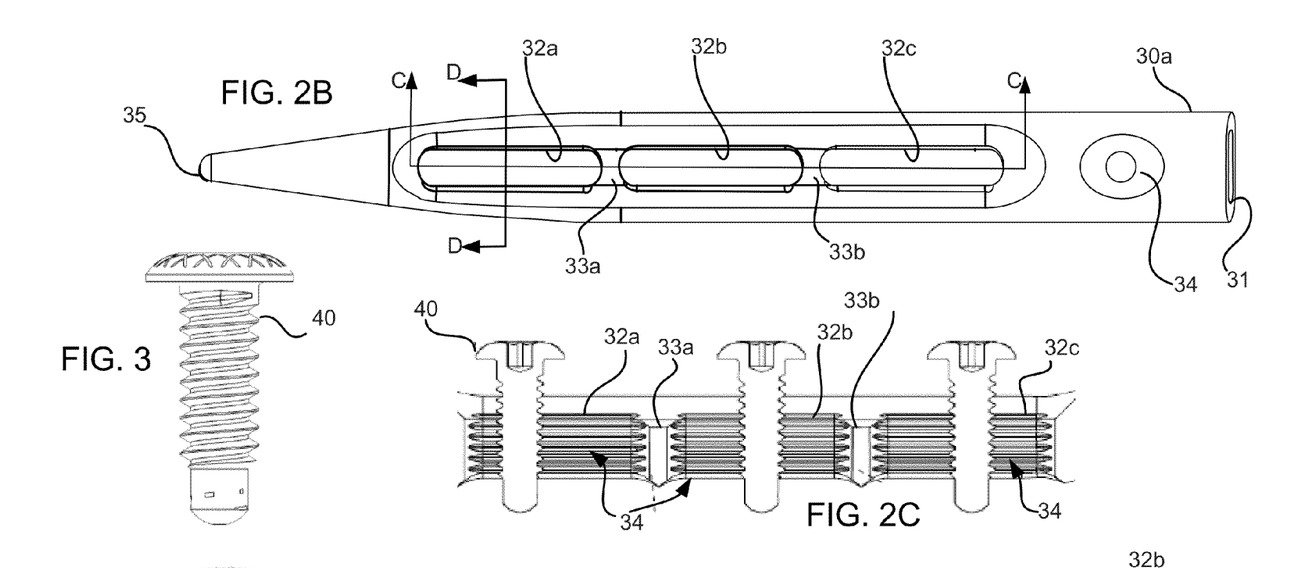
FIG. 2B is a top plan view of the portion of an endosteal nail plate of FIG. 2A.
FIG. 2C is a partial, cut-away view of the endosteal nail plate of FIG. 2B taken in the direction of arrows C-C, and including locking machine screws in the slots thereof.
FIG. 3 is an enlarged, side elevation view of a locking machine screw that can be used with the device of FIG. 2.
Figure 2D:
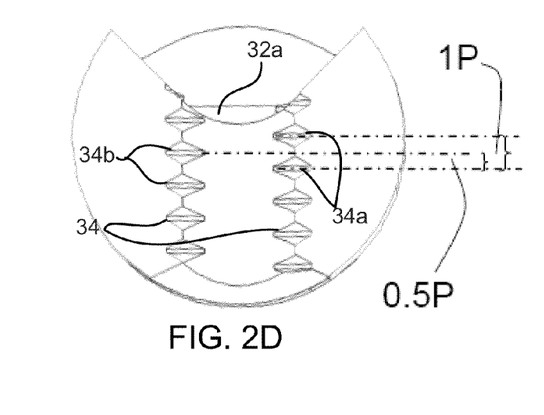
FIG. 2D is a partial, cut-away, view of the endosteal nail plate of FIG. 2B taken in the direction of arrows D-D.
Figure 2E:
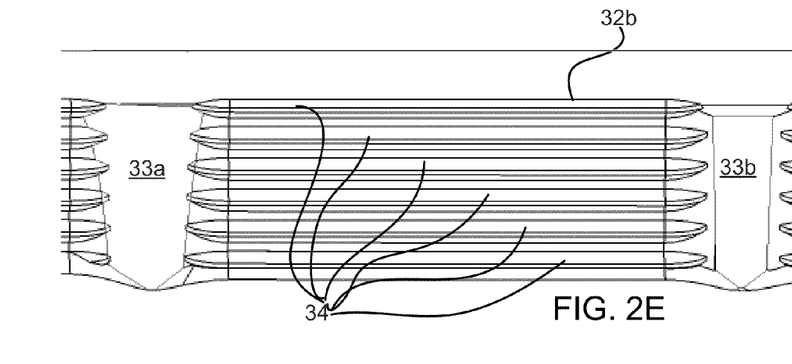
FIG. 2E is an enlarged view of a portion of the partial, cut-away view of FIG. 2C, without the screw included in FIG. 2C.

In order to insert a locking screw into a slot 32, and simultaneously engage the slot 32, the profile of the grooves in the slot 32 of FIGS. 2C-2E must be configured to accommodate the helical thread of the screw. As noted above, the slots 32 are threaded for engagement with screws, such as locking machine screws 40. In particular, the at least 2 grooves on each of the two opposing parallel side walls of longitudinal slot 32 are disposed parallel to the longitudinal axis of first nail portion 30a and are configured to match the shape and the pitch of the threads of screws 40.

The threaded grooves cut or formed in the slots 32 of the ENP 30 are preferably oriented in the longitudinal direction of desired adjustment in order to permit the ENP 30 to be advanced distally or proximally without loosening during such adjustment. Upon completion of the slotted adjustment, the screws 40 can be fully tightened within the threaded slots 32a, 32b, 32c of the ENP 30, thus fixing the ENP 30 in the bone at the desired position.

FIG. 2C shows a cross-section of the threaded slots 32 taken in the direction of the arrows C-C, while FIG. 2D shows a cross-section of a threaded slot 32a in accordance with the instant invention taken in the direction of the arrows D-D. In one particular embodiment the threads 34a on one side of the threaded slot are vertically displaced (i.e., offset) by one-half of the pitch P of the thread relative to the threads 34b on the opposite side of the threaded slot 32, as shown more particularly in FIG. 2D.

This relative displacement of opposite side grooves permits the stable engagement of the threads of screws 40 into the side wall grooves of slot 130 at the tangential contact points of the aforementioned threads with the grooves, while still permitting the loosely engaged screws 40 to be displaced horizontally along the length of the slots. Complementarily, once the screws are held in a fixed position (for example, by having been inserted into holes drilled in a bone cortex) the slot 32

(and consequently, the totality of the first nail portion 30a) may be displaced longitudinally through a range of positions along the axis of the slots, until such time as the surgeon wishes to fix the nail 30 at a final desired location by further tightening of the screws.

It should be noted that, when screws 40 are tightened by clockwise rotation, such rotation will cause the thread of the screws to pull, draw or lag the grooved longitudinal slot 32 (and consequently, the totality of the first nail portion 30a) towards the heads of the screws. Therefore, any matter, such as a bone cortex, that is interposed between the screw heads and the first nail portion 30a will be tightly clamped between the aforementioned screw heads and the upper surface of the first nail portion 30a.

Referring more particularly to FIGS. 2-4B, there is shown an ENP 30, inserted into an intramedullary canal 12 of a bone, in accordance with one particular embodiment of the instant invention. As indicated hereinabove, the ENP 30 of the instant embodiment is formed as a single piece, and includes a least one screw hole on one end and at least one threaded slot on the opposite end. In such a case, the ENP 30 is inserted into the bone, as shown in FIG. 4A, either through one end of the bone, or by displacing the bone segments 15, 16 to insert the ENP 30 into the intramedullary cavity 12. Screws 40a and 40b are fixedly locked through holes in a first segment 15 of the bone into holes 36 in the corresponding portion 30c of the ENP 30. Additionally, locking screws 40c, 40d and 40e are loosely inserted through holes drilled in a second segment 16 of the bone (i.e., which second segment is separated from the first segment by, e.g., a fracture, break or osteotomy 10a) and into the threaded slot(s) 32 of the ENP 30, as shown in FIG. 4A. Holes in the bone segments may be drilled in the appropriate location with the aid of a jig or guide (not shown).

Figure 4A:
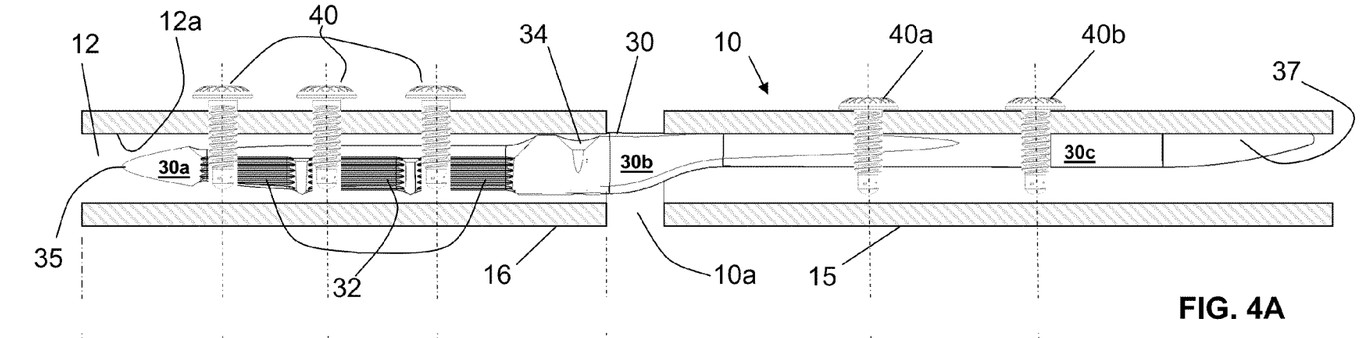
FIGS. 4A and 4B are cut-away views of the endosteal nail plate of FIG. 2, in sequential stages of installation in a fractured or osteotomized bone.
Figure 4B:
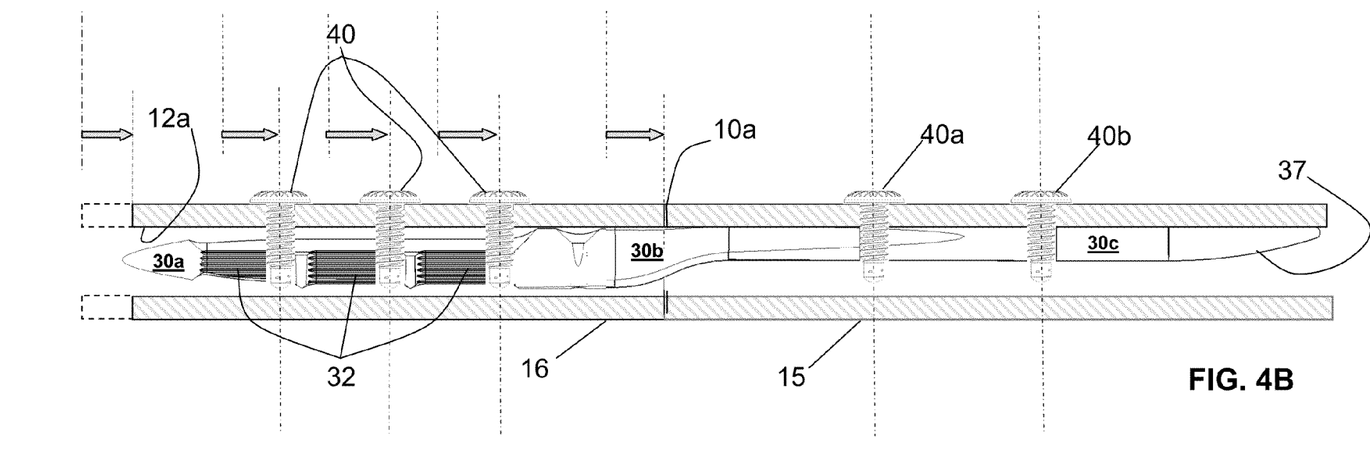
Figure 5:
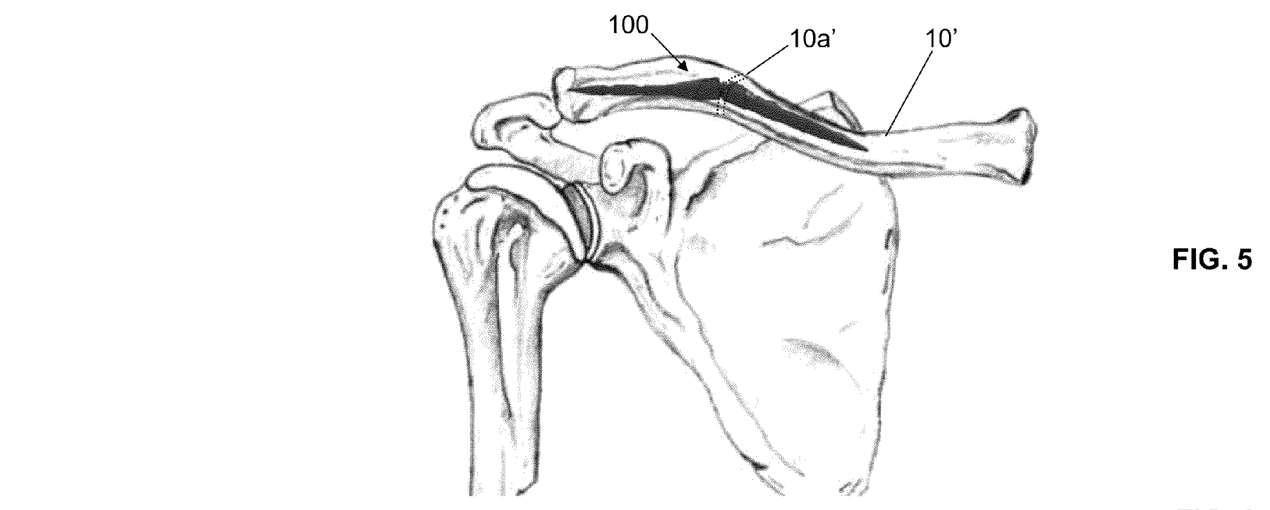
FIG. 5 is a diagrammatic view of an endosteal nail plate for the clavicle in accordance with another particular embodiment of the present invention.
Figure 6:
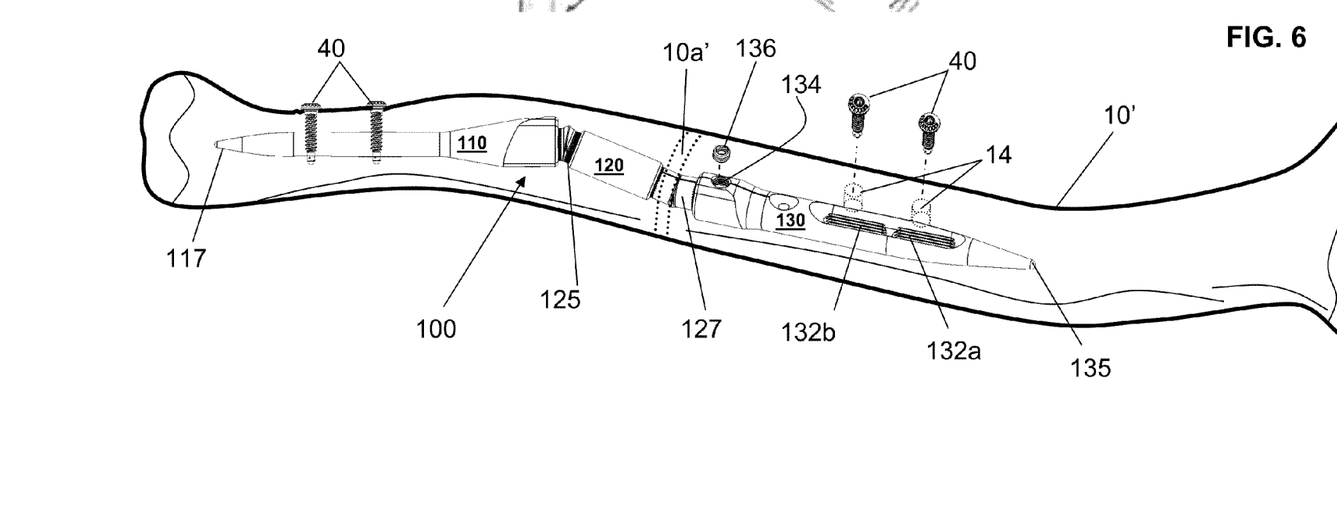
FIG. 6 is a further diagrammatic enlarged view of the endosteal nail plate of FIG. 5 where the clavicle bone is shown transparent.
Figures 7A, 7B, 7C, 7D:
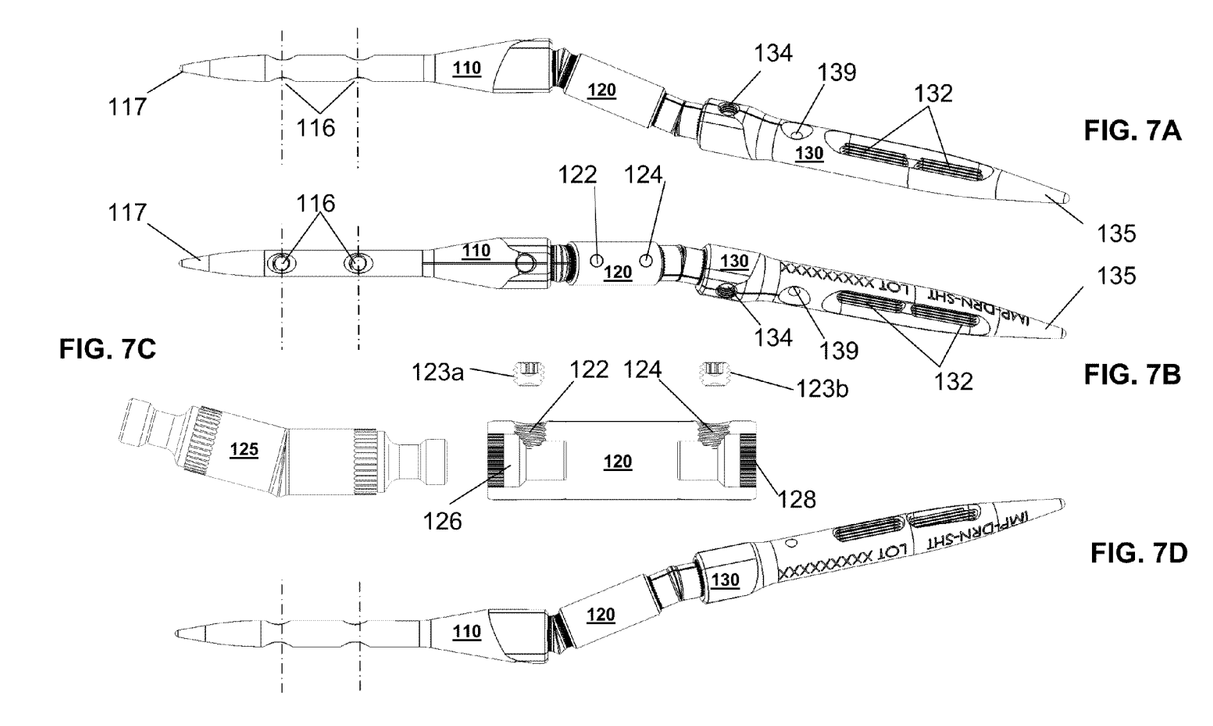
FIGS. 7A-7B and 7D-7F are perspective views from different viewpoints of the endosteal nail plate of FIG. 5 further detailing the component parts.
FIG. 7C is an enlarged elevational view of an angled connector and a cross sectional view of a short segment, both of which are component parts of the endosteal nail plate of FIG. 5.
Figure 7E:
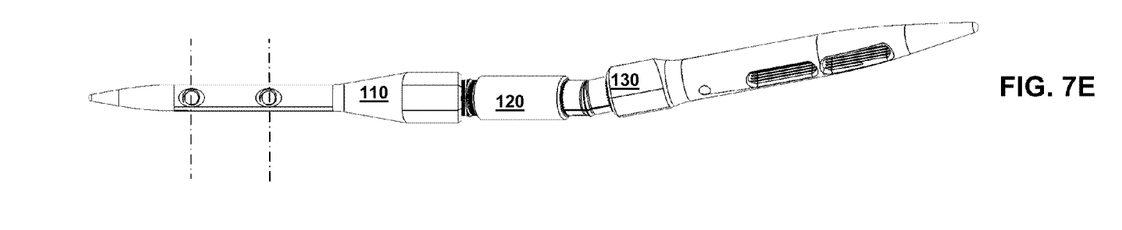
Figure 7F:
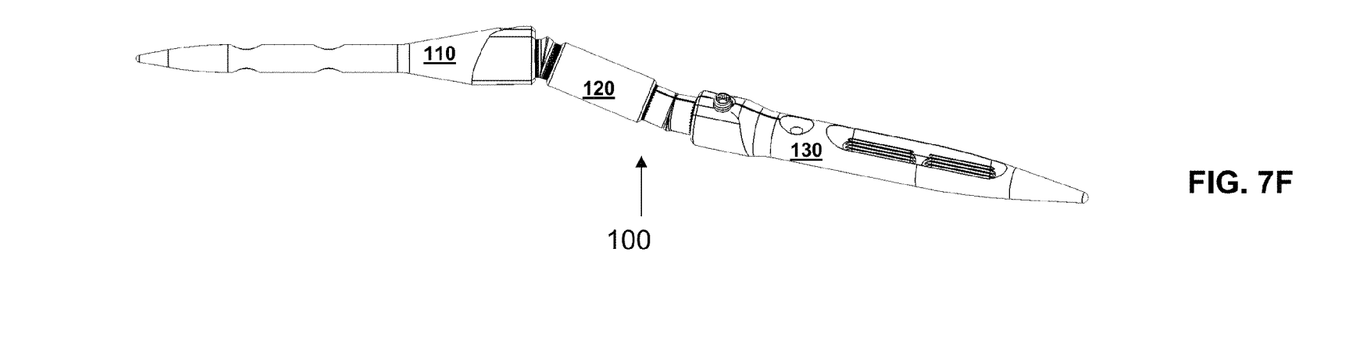
Figure 7G:
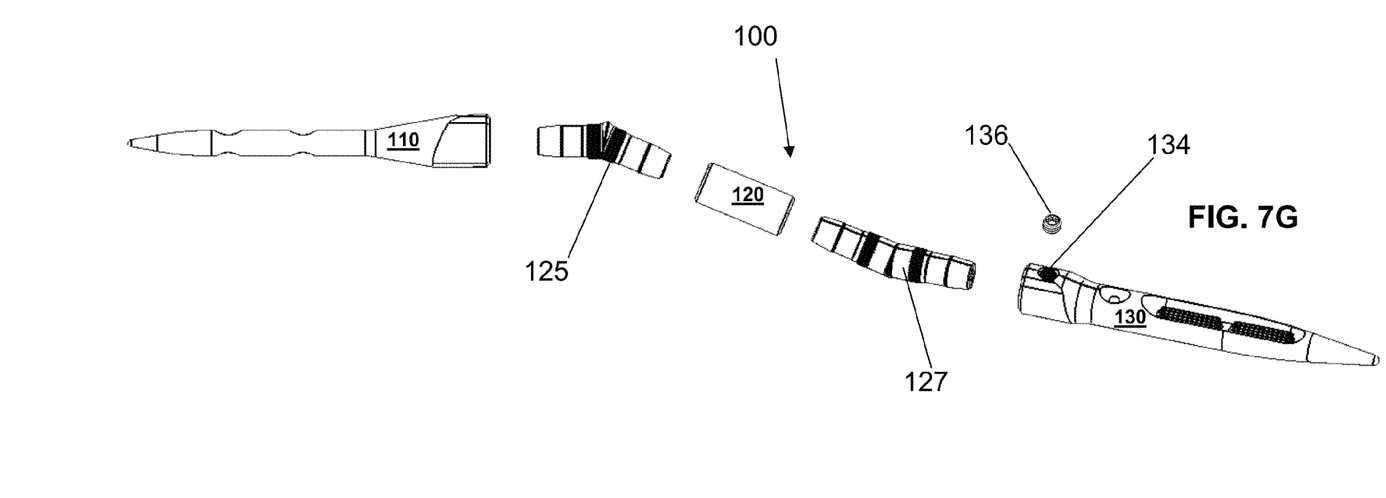
FIG. 7G is an exploded perspective view of component parts of the endosteal nail plate of FIG. 5.

An adjustment procedure (i.e., reduction) can then be performed wherein the second bone segment 16 is shifted towards the first bone segment 15 in the direction of the arrows shown in FIG. 4B, to contact or approximate the ends of the first and second bone segments as desired, during which procedure the screws 40c, 40d and 40e in the threaded slot(s) 32 slide longitudinally within the threaded slot(s) 32. Once the adjustment/reduction has been performed, the screws 40c, 40d and 40e in the threaded slot(s) 32 of the ENP 30 are tightened (as can be seen from FIG. 4B), thus firmly locking the ENP 30 and bone segments 15, 16 in the desired relationship.

Figures 13, 13A:
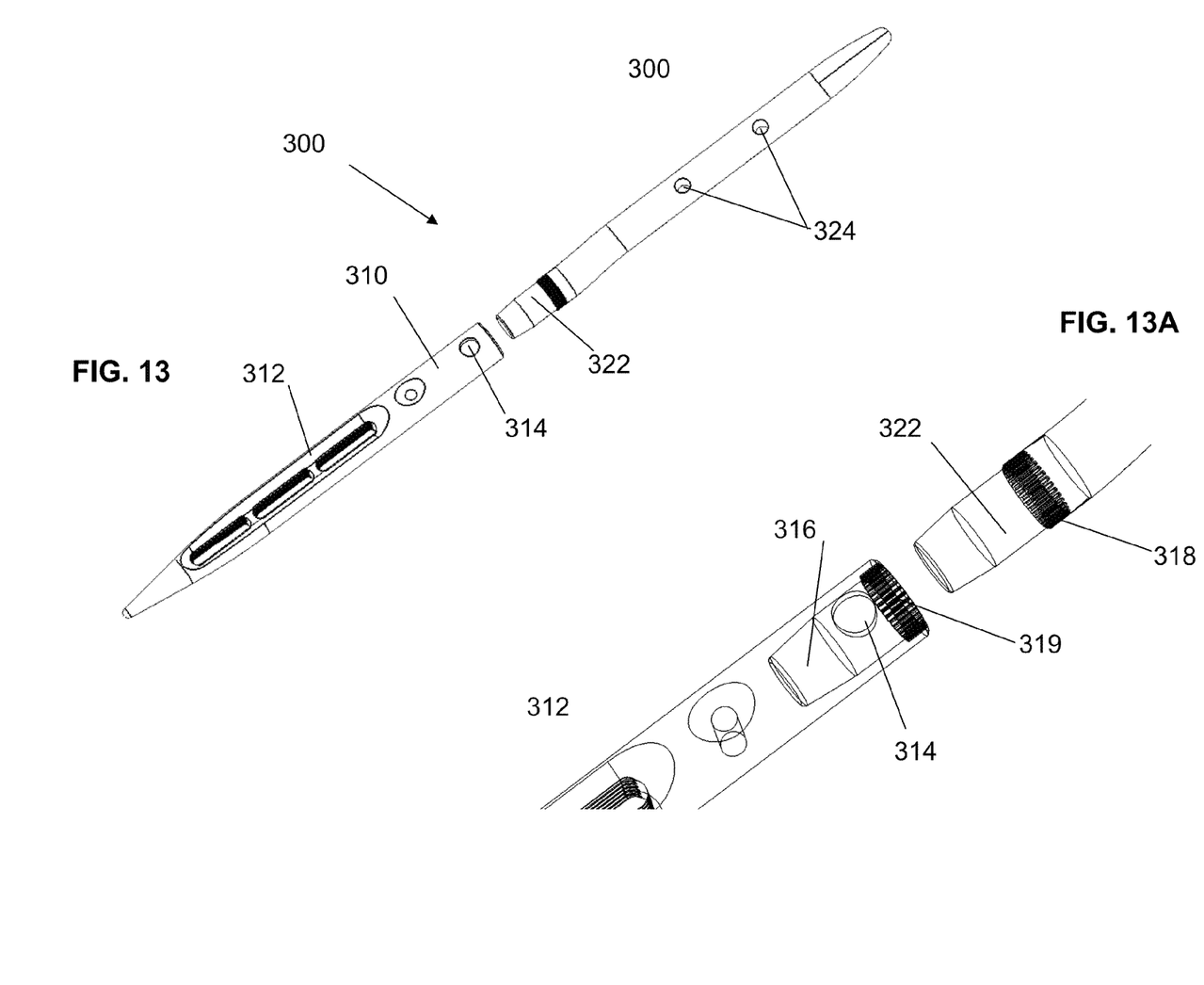
FIG. 13 is an exploded perspective view of a two segment endosteal nail plate in accordance with another embodiment of the instant invention.
FIG. 13A is an enlarged perspective view of the two segment endosteal nail plate of FIG. 13.
Figure 14A:
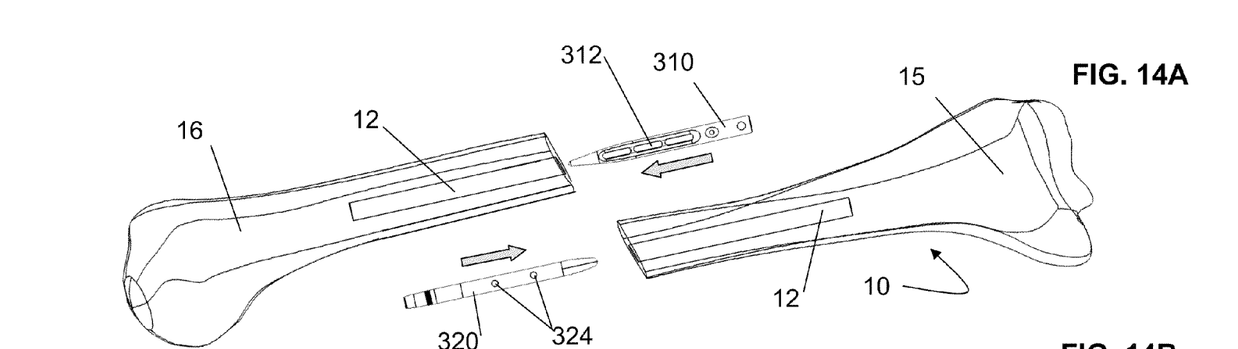
FIG. 14A-14C are diagrammatic cut-away views of the two segment endosteal nail plate of FIG. 13 in subsequent steps of installation in a fractured or osteotomized bone.
Figure 14B:
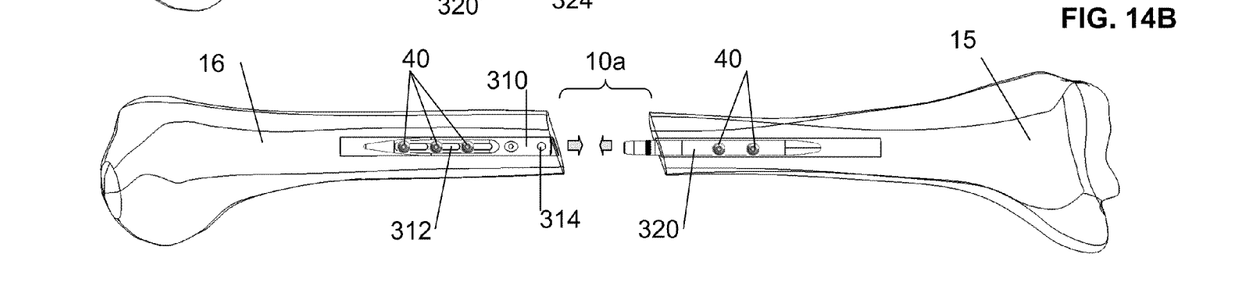
Figure 14C:
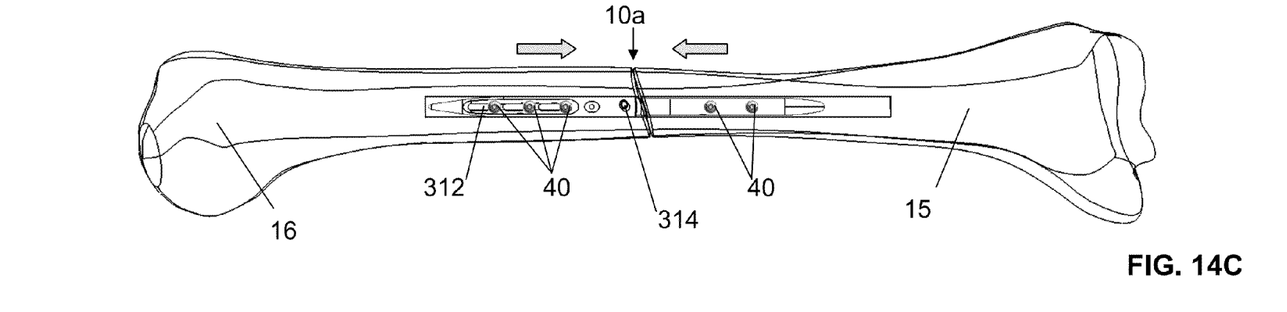

As noted hereinabove, the ENP 30 can be integrally formed as a single unit, as described in connection with FIGS. 2-4B, or may be formed as two or more separable parts that can be connected together to form a fixation device. Referring now to FIGS. 13-14C, another embodiment of the invention is shown wherein a two piece ENP 300 is provided. The ENP 300 is similar in most respects to the ENP 30, except that the first portion 310 (corresponding to 30a of FIG. 2) is formed as a first piece separate from, but connectable to, the second portion 320, which has a connecting portion 322 formed at one end thereof. The connecting portion 322 is configured to be mated to a complementary portion 316 on the first portion 310. In the example shown, the connecting portion 322 includes a male connector that is sized to closely mate with a female connecting portion 316 within the body of the first portion 310. However, the reverse can be true, if desired (i.e., the first portion 310 could include a male connector that matingly engages a female connector in the connecting portion).

The two portions 310, 320 may be fixed together by a set screw inserted through the threaded hole 314 and tightened against connecting portion 322 disposed at the proximal end of the second portion 320, and received within the first portion 310. Additionally, if desired, complementary splines 318 and 319 can be provided in connecting portions 322 and 316 to lock the rotational positions of the first portion 310 and second portion 320 relative to one another, once the two portions have been engaged.

Advantageously, such a two piece ENP 300 can be assembled at the site of the fracture, instead of requiring insertion from one end of the bone. More particularly, as can be seen from FIGS. 14A-14C, the two piece ENP 300 can be used to fix two bone segments relative to one another, according to the following method.

First, as shown in FIG. 14A, each of the first and second ENP portions 310, 320 are inserted into portions of the intramedullary cavities 12 of corresponding bone segments 15, 16. Note that, if desired, a kit including a plurality of different first and second ENP portions 310, 320 of varying shapes, lengths and diameters may be provided to accommodate different anatomies during surgery.

Once the portions 310 and 320 have been selected and inserted, as shown more particularly in FIG. 14B, screws 40 are inserted through holes pre-drilled in the bone segment 15 and tightened to engage the threaded holes 324 of portion 320. Thereafter, screws 40 are inserted through pre-drilled holes in bone segment 16 to loosely engage the threads or grooves formed in the sidewalls of the threaded slots 312 of ENP portion 310. Subsequently the two ENP portions 310, 320 are matingly engaged to one another at a desired rotational angle, as determined by the alignment of the splines contained in the two portions of the ENP 300. The ENP 300, once assembled in the two bone segments 15, 16 can be fixed together by tightening a set screw through hole 314.

As can be seen from FIG. 14C, after the ENP 300 has been assembled, the fracture can be reduced by moving the bone segments 15, 16 towards one another (i.e., in the direction of the arrows of FIG. 14C). This movement is allowed by virtue that the screws 40 can slide longitudinally along the elongated, threaded slots 312. Once the fracture has been reduced, the screws 40 in threaded slots 312 are tightened, thereby holding the two bone segments 15, 16 in close contact relative to each other, a necessary condition to permit healing of the fracture or osteotomy.

Referring now to FIGS. 5-7G, in another particular embodiment of the invention, the ENP can be modular, having separable and/or configurable sections that could accommodate various anatomies. For example, a configurable ENP 100 would be especially useful for curved bones, such as the clavicle 10', which has several bends in 2 planes. In particular, a modular ENP 100 could be configured to join various different angular parts, thus accommodating different patient and bone variations. In particular, various linear sections or segments (e.g. segments 110, 120, 130 of FIG. 6) of an ENP 100 can be interconnected by straight or angled connectors, such as angled connectors 125 and 127. It should also be appreciated that a similar solution could be accomplished using straight or angled connectors between ENP segments, wherein one or more of the ENP segments are curved.

The segments 110, 120, 130, can be connected to together at their desired relative orientations by engaging splines on the connectors 125, 127 with complementary splines on the segments 110, 120, 130. Thus, the angled connectors 125, 127 can be used to connect the segments 110, 120, 130 in varying geometries. The final configuration of the ENP 100 can be fixed by securing the connectors to the respective segments using set screws, such as the set screws 123a, 123b and 136. Each set screw 123a, 123b, 136 engages a threaded hole 114, 122, 124, 134 through a wall of one of the segments to press against a neck of an inserted connector 125, 127, thus fixing the head of the connector 125, 127 in a mating female connection, such as in the chambers 126 or 128 of FIG. 7C. However, this configuration is not meant to be limiting. It should be understood that the arrangement of the male and female connectors can be reversed from that shown in FIGS. 7A-7G, if desired. Further, in one particular embodiment, the male connector is formed as part of one or more of the segments of the modular ENP 100. However, in a further embodiment of the invention, the connector can include a male or female end at each of two ends, thus being configured to mate with a corresponding female or male end at each of the two modular ENP segments, and fixed therein by a set screw.

As previously described in connection with the one piece ENP 30 of FIGS. 2-4, one or more holes 116 can be provided in one of the portions 110, for tightly securing the ENP portion 110 to the bone in the intramedullary cavity. Additionally, at least one threaded slot 132, such as the slots 132a and 132b, are provided in one or more of the ENP segments 110, 120, 130 of a modular ENP 100, to increase adjustability during reduction of the fracture, as described hereinabove. As with the embodiment described hereinabove in connection with FIGS. 13-14C, the ENP 100 can be assembled at the site of the fracture.

Figures 10, 11, 12:
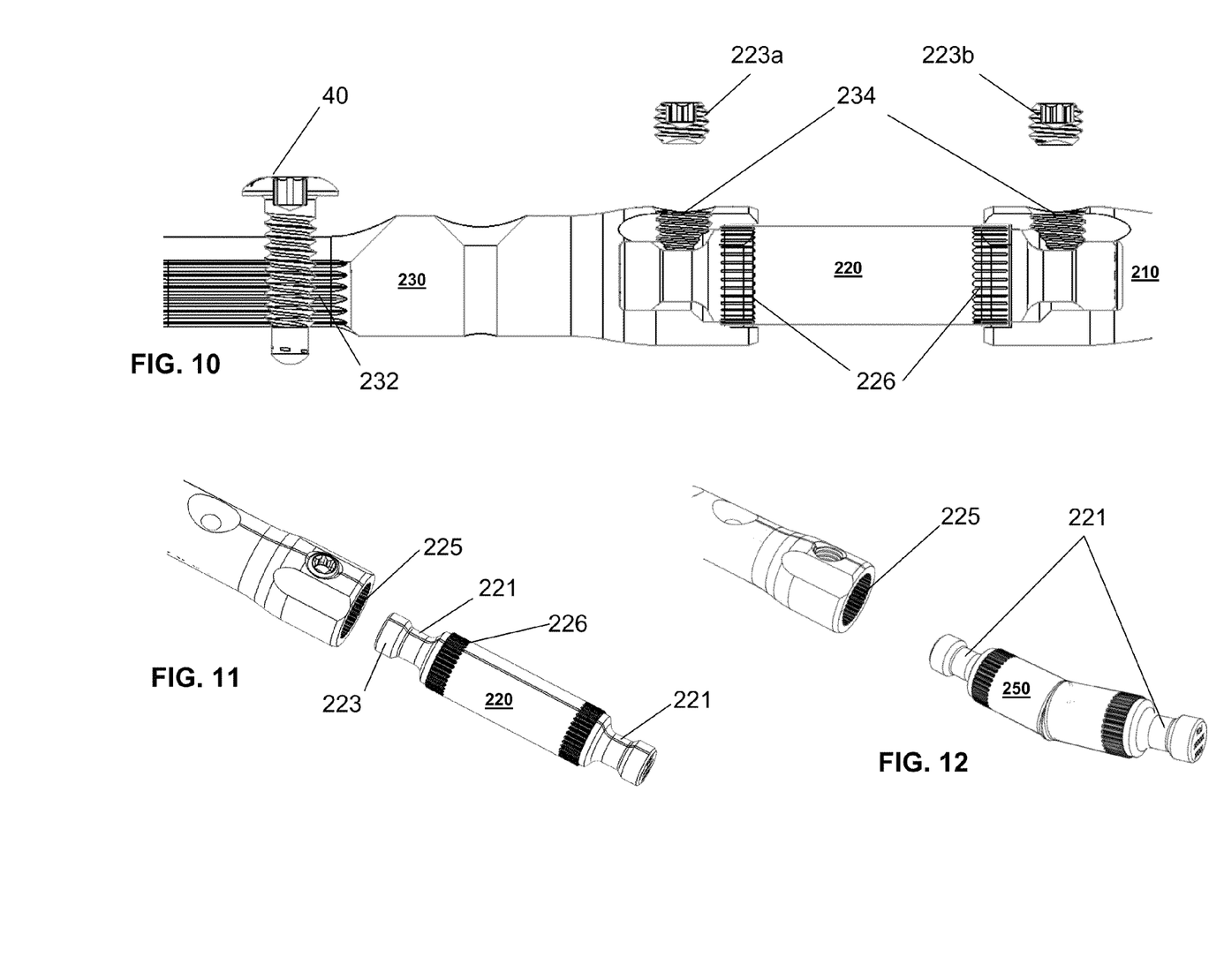
FIG. 10 is an enlarged cross sectional view of a segment and a connector of an endosteal nail plate in accordance with a further embodiment of the instant invention.
FIGS. 11-12 are exploded perspective views of a segment and a connector of the endosteal nail plate of FIG. 10.

Referring now to FIGS. 10-12, there are shown further connectors or coupling pieces 220, 250 that can be used to connect various modular segments together, in accordance with other preferred embodiments of the invention. In particular, the connectors 220, 250 can be used in any embodiment of the invention provided herein that utilizes a set screw to connect two or more ENP segments together.

More particularly, the connectors 220, 250 of FIGS. 10-12 are used to engage and secure a first portion 230 of an ENP to a second portion 210. In one particular embodiment of the invention, the portion 230 is functionally equivalent to the portion 310 of FIG. 13, while the distal section of the portion 210 is functionally equivalent to the distal section 320 of the ENP 300 of FIG. 13. Note however, in the present embodiment, the connecting portion 322 of FIG. 13 is be replaced by a complementary female connector, as shown.

More particularly, as can be seen from FIG. 10, the first portion 230 may include one or more longitudinal threaded slots 232, having two opposing, grooved parallel side walls. The first portion 230 additionally includes an internally splined head portion 225 configured to engage the externally splined portion 226 of a connector 220, 250. Extending through the internally splined head portion 225 is a threaded hole 234 adapted to receive a set screw 223a. In the present embodiment, set screw 223a is chosen to be a correspondingly threaded headless set screw, although other types of screws can be used. As more clearly seen in FIG. 10, the axis of threaded hole 234 is perpendicular in relation to the longitudinal axis of the first portion 230, but may also be oblique to that axis, as desired.

As can more clearly seen in FIG. 11-12, the connector portions can be straight 220 (i.e., concentrically surrounding an axis extending through the length of the proximal nail portion), curved or angled 250 (i.e., at an angle to the axis extending through the length of the mating nail portion) and may be provided in a plurality of lengths and curvatures or angles. The connector portions include, at each end, heads or lugs 223 intended to be inserted into heads 225 of the first and second nail portions 230, 210, respectively, and to be firmly attached to heads 225 upon tightening of set screws 223a, 223b.

If a straight connector is selected, the first and second nail portions 230, 210, will be aligned in the same (neutral) axis; however, if curved or angled connectors are selected the corresponding axes of portions 230 and 210 will be at an angle with respect to each other. It should be noted that by rotating the selected curved or angled connectors before inserting the lugs 223 of the connectors into heads 225 of portions 230, 210, the corresponding splines 226 can be engaged in a plurality of positions. This plurality of positions can be described as a "cone" of possible positions of the axis of first portion 230 relative to the axis of second portion 210.

In one particularly preferred embodiment of the invention, there is provided a non-traditional spline for use in fixing the orientation of the ENP after angulation and/or rotation. In accordance with one particular embodiment of the invention, the connector portions for an ENP include Vernier or Nonius splines to aid in fixing the ENP segments relative to one another at desired angles. One characteristic of a Nonius spline is that only a few teeth of one part need engage the teeth of a second part. By selecting the correct staggering of the teeth on each part, it is possible to increase the total possible number of engagement combinations thus allowing for a finer rotational adjustment. This design is especially useful in small size devices, where the number and/or size of traditional splines may be limited by manufacturing constraints.

Figure 8:
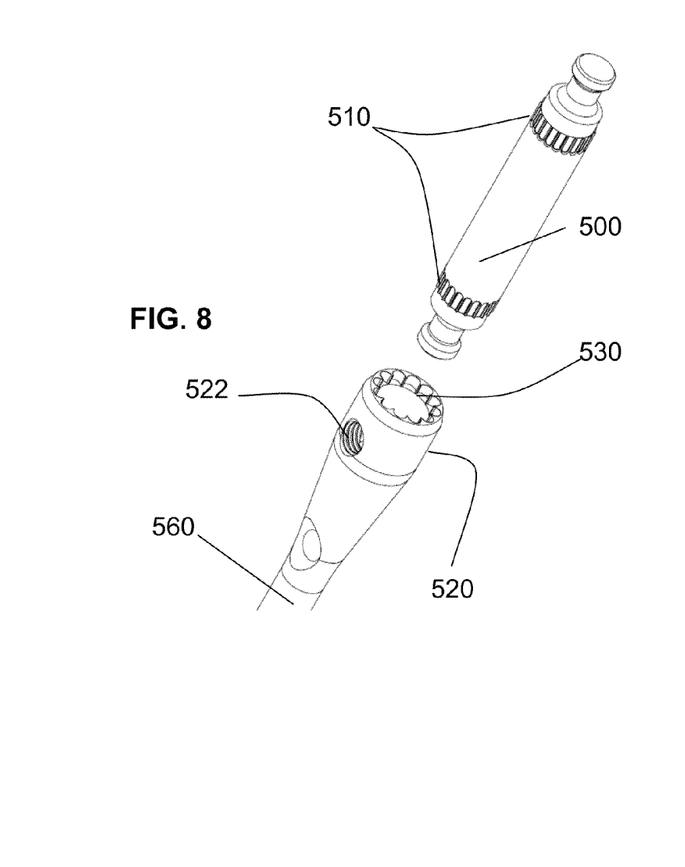
FIG. 8 is a perspective view of another particular embodiment of a connector and a segment of an endosteal nail plate where the number of splines in the connector differs from the number of splines in the segment.
Figure 9A:
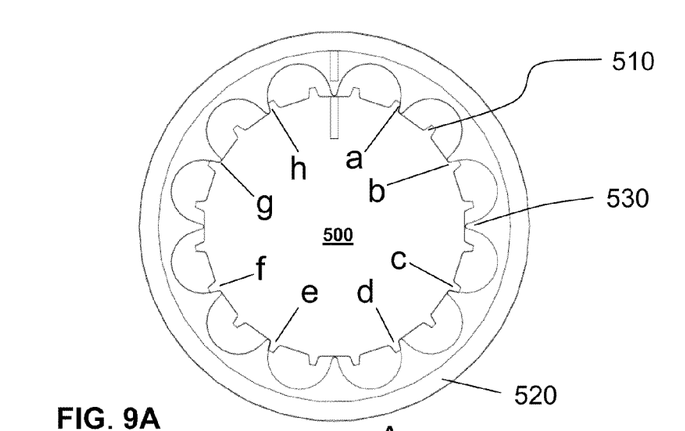
FIG. 9A-9B are diagrammatic sectional views of the relative position of splines in the connector and the segment of the endosteal nail plate of FIG. 8 before and after clockwise rotation of the connector relative to the segment.
Figure 9B:
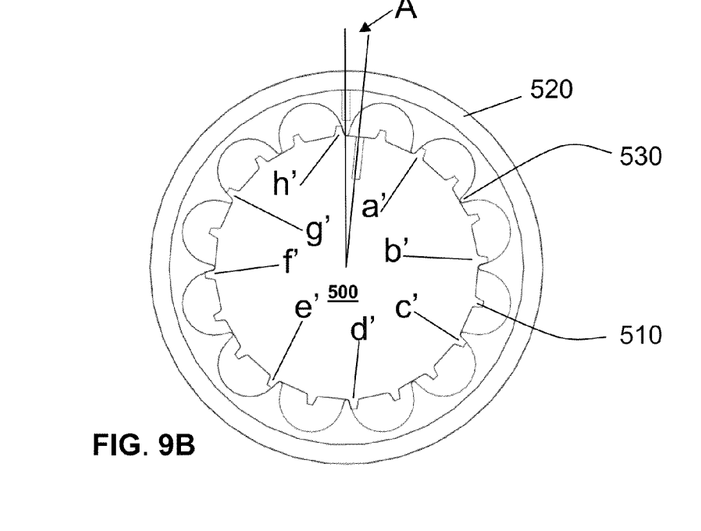

Referring now to FIGS. 8-9B, there is shown a particular embodiment of the splines 530 in head 520 of first portion 560 and the corresponding splines 510 of a connector 500, wherein the splines are Nonius splines. In this particular embodiment there are shown twelve splines 530 in head 520 of a first ENP portion 560 and twenty splines 510 in connector portion 500. This differentiation in the number of head splines relative to connector splines is advantageous as it provides more rotational adjustability. If the number of splines in both the head and the connector were identical, for example, twelve in each, the rotational adjustability of the connector relative to the head would be in steps of 30 degrees each. However from any initial position, as illustrated in FIG. 9A, the twenty splines 510 in the connector 500 engage the twelve splines 530 in the head 520 at points a, b, c, d, e, f, g and h. The rotational adjustability of the connector relative to the head is in steps of angle A, in this case 6 degrees each, instead of 30 degrees with traditional splines and the new points of engagement of splines 510 in the connector 500 with splines 530 in the head 520 would be at points a', b', c', d', e', f', g' and h' (FIG. 9B).

It should be noted that the particular number of splines 530 in the head 520 and 510 in the connector 500, illustrated herein, is not intended to be limiting since different number of combinations exist that provide different degrees of rotational adjustment with a corresponding increase or reduction in the number of spline engagement points. The minimum number of splines is two in the head 520 and one on the connector 500 (or vice-versa), which provides engagement but eliminates the rotational adjustability. It should be understood that a similar arrangement of Nonius splines can be provided in any combination of head portions and connector portions of any of the embodiments described herein.

In an alternate embodiment of the invention, the connection between modular ENP segments can be retained using a different mechanism. For example, as shown in FIG. 15, a tensioned cable 410 could be used to maintain the connection between different module segments of ENP 400, thus retaining the segments relative to one another at a desired angle without necessitating the use of a set screw.

Figure 15:
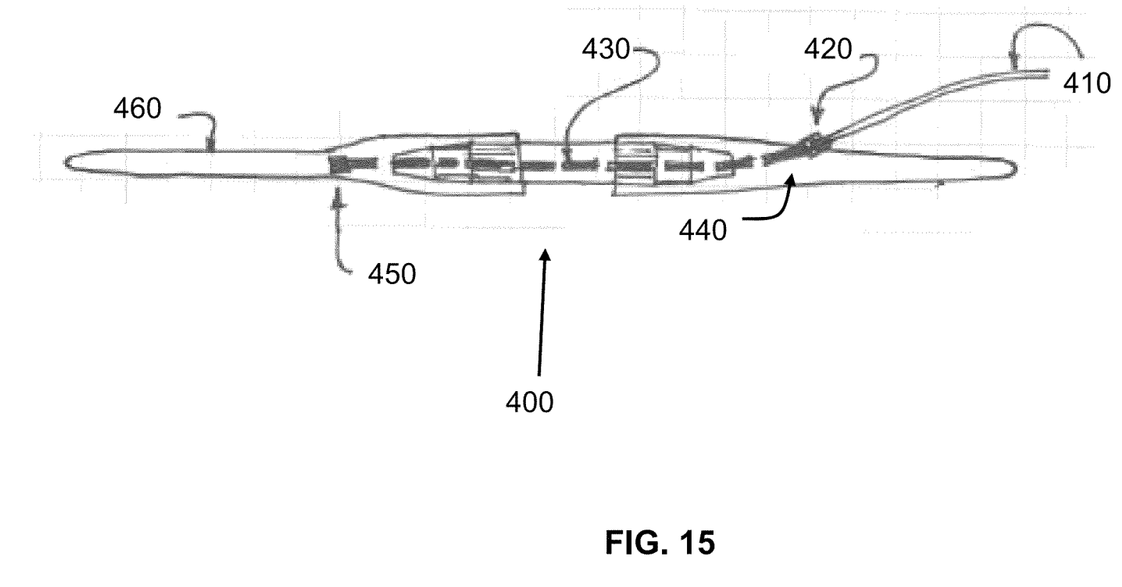
FIG. 15 is a top plan view of an endosteal nail plate in accordance with a further embodiment of the present invention.

As can be seen from FIG. 15, the use of a tensioned cable 410 to retain the connector 430 between two modular ENP segments 440, 460, would provide for a lower profile, enabling its use in ENPs of very small nail diameters, and could possibly be easier to install than a set screw. As shown, once tensioned, a crimp 420 could be used to secure the ENP configuration at the proper tension and orientation (i.e., which may, again, use splines as described elsewhere herein).

Referring more particularly to the particular embodiment illustrated in FIG. 15, a cable 410 is anchored within one of a plurality of modular ENP segments 430, 440 and 460. The cable 410 passes through a connector 430 between the first ENP segment 460 (to which the cable is anchored at 450) and a second ENP segment 440, exiting through a recessed pocket in the second ENP segment 440. A crimp 420 can then be passed down the "Bitter End" of the cable. A special tool can be used to pull the cable, thus joining together and tensioning the separate segments and connector of the modular ENP 400, and the crimp can be crimped to maintain the tension, thus securing the construct. Excess cable (i.e., the "Bitter End") can then be removed by trimming.

In a further embodiment of the invention, a similar construct to that disclosed herein could be achieved using a small threaded, flexible rod that would serve a similar purpose to the cable described in connection with FIG. 15. Such a rod could, if desired, be made from a material such as surgical steel and/or nitinol.

Although the invention is illustrated and described herein, various modifications and structural changes may be made therein without departing from the spirit of the invention and within the scope and range of equivalents of the claims.

What is claimed is:

1. An endosteal nail plate for fixing segments of a bone, comprising:
    a first portion for insertion into a first segment of a bone;
    a second portion for insertion into a second segment of the same bone;
    said first portion including at least one screw hole located therethrough; and
    said second portion including at least one threaded, elongated slot located therethrough, said at least one elongated slot including two opposing, grooved parallel side walls, the grooves on each of said parallel side walls having a shape and a pitch configured to match said shape and pitch of said fastener, all of said grooves being disposed parallel to each other and parallel to the longitudinal axis of the second portion, and wherein the grooves on a first of said parallel side walls are vertically displaced one-half of said pitch relative to the grooves on the second, opposite, side wall.

2. The endosteal nail plate of claim 1, wherein said first portion and said second portion are formed as separate pieces that are joinable by a connecting portion.

3. The endosteal nail plate of claim 2, wherein the connecting portion is a separate piece connectable between said first portion and said second portion.

4. The endosteal nail plate of claim 2, wherein the portions are fixable at a particular angle relative to one another using splines located on said connecting portion and on at least one of said first portion and said second portion.

5. The endosteal nail plate of claim 4, further including a third portion for insertion into the same bone, said third portion fixable between said first portion and said second portion at a particular angle relative to said first portion using a second connecting portion and at a particular angle relative to said second portion using a third connecting portion, the portions being fixable at a particular angle relative to one another using splines.

6. A method for fixing two or more segments of a bone, comprising:
    a) providing the endosteal nail plate of claim 1;
    b) inserting the endosteal nail plate into a bone with the first portion being located in a first bone segment and the second portion being located in a second bone segment;
    c) securing the first portion to the first bone segment by passing a body of at least one first screw through a portion of said first bone segment and into said at least one screw hole and tightening said first screw;
    d) passing a body of at least one second screw through a portion of said second bone segment and into said at least one threaded, elongated slot to slidably engage a thread of said second screw with a thread of said at least one threaded, elongated slot;
    e) after steps c) and d), moving at least one of the first and second bone segments towards the other one to dispose the first bone segment in contact with the second bone segment; and
    f) after step e) tightening the at least one second screw in said elongated slot to fix said second portion to said second bone segment.

7. The method of claim 6, wherein said first portion and said second portion are formed as separate pieces that are joinable by a connecting portion, and wherein said inserting step includes the steps of:
    b1) inserting said first portion into said first bone segment;
    b2) inserting said second portion into said second bone segment; and
    b3) after steps b1) and b2) securing said first portion to said second portion.

8. The method of claim 7, wherein said inserting step further includes the step of:
    b4) after steps b1) and b2), and before step b3), joining said first segment to said second segment at a particular angle relative to one using said connecting portion.

9. The method of claim 8, wherein said connecting portion includes splines that matingly engage with splines on at least one of said first portion and said second portion.

10. An endosteal nail plate for fixing a bone, comprising:
    a first portion for insertion into a first segment of a bone;
    a second portion for insertion into a second segment of the same bone;
    said first portion including at least one screw hole located therethrough;
    said second portion including at least one threaded, elongated slot located therethrough, said at least one elongated slot including two opposing, grooved parallel side walls, the grooves on each of said parallel side walls having a shape and a pitch configured to match said shape and pitch of said fastener, all of said grooves being disposed parallel to each other and parallel to the longitudinal axis of the second portion, and wherein the grooves on a first of said parallel side walls are vertically displaced one-half of said pitch relative to the grooves on the second, opposite, side wall; and
    a third portion for insertion into the same bone, said third portion connectable between said first portion and said second portion.

11. The endosteal nail plate of claim 10, wherein said third portion is a connector for connecting said first portion to said second portion.

12. The endosteal nail plate of claim 11, wherein the connector is a straight connector.

13. The endosteal nail plate of claim 12, wherein the connector is an angled connector.

14. The endosteal nail plate of claim 13, wherein said connector includes splines engageable with splines on at least one of said first portion and said second portion to fix said first portion at a particular, non-zero angle relative to said second portion.

15. The endosteal nail plate of claim 10, wherein the third portion is connected between said first portion and said second portion by a first angled connector and a second angled connector, such that said first portion is fixed relative to the third portion at a first, non-zero angle and said second portion is fixed relative to said third portion at a second non-zero angle.

16. The endosteal nail plate of claim 15, wherein the bone is a curved bone having bends in two or more planes.

17. The endosteal nail plate of claim 16, wherein the curved bone is a clavicle.

18. A method for fixing two or more segments of a bone having bends in two or more planes, comprising the steps of:
   a) providing the endosteal nail plate of claim 15;
   b) assembling the provided endosteal nail plate at the site of a fracture;
   c) securing the first portion to the first bone segment by passing a body of at least one first screw through a portion of said first bone segment and into said at least one screw hole and tightening said first screw;
   d) passing a body of at least one second screw through a portion of said second bone segment and into said at least one threaded, elongated slot to slidably engage a thread of said second screw with a thread of said at least one threaded, elongated slot;
   e) after steps c) and d), moving at least one of the first and second bone segments towards the other of the first and second bone segments to dispose the first and second bone segments adjacent to one another; and
   f) after step e) tightening the at least one second screw in said elongated slot to fix said second portion to said second bone segment.

19. The endosteal nail plate of claim 18, wherein the bone is a clavicle.

20. The endosteal nail plate of claim 18, wherein the first and second angled connectors include splines engageable with splines on said third portion and on said first portion and said second portion to fix each of said first portion and said second portion at a particular, non-zero angle relative to said third portion.

* * * * *